(12) United States Patent
Jafari et al.

(10) Patent No.: US 9,273,006 B2
(45) Date of Patent: Mar. 1, 2016

(54) ANABOLIC COMPOUNDS FOR TREATING AND PREVENTING BONE LOSS DISEASES

(71) Applicant: SYDDANSK UNIVERSITET, Odense M (DK)

(72) Inventors: Abbas Jafari, Odense V (DK); Li Chen, Odense M (DK); Moustapha Kassem, Odense M (DK); Basem Abdallah, Odense M (DK)

(73) Assignees: SYDDANSK UNIVERSITET, Odense M (DK); REGION SYDDANMARK, Vejle (DK)

( * ) Notice: Subject to any disclaimer, the term of this patent is extended or adjusted under 35 U.S.C. 154(b) by 0 days.

(21) Appl. No.: 14/399,726

(22) PCT Filed: May 3, 2013

(86) PCT No.: PCT/EP2013/059207
§ 371 (c)(1),
(2) Date: Nov. 7, 2014

(87) PCT Pub. No.: WO2013/167475
PCT Pub. Date: Nov. 14, 2013

(65) Prior Publication Data
US 2015/0126548 A1    May 7, 2015

Related U.S. Application Data

(60) Provisional application No. 61/644,046, filed on May 8, 2012.

(30) Foreign Application Priority Data

May 8, 2012 (DK) ................................ 2012 00320

(51) Int. Cl.
*C07D 217/04* (2006.01)
*A61K 31/472* (2006.01)
*A61K 45/06* (2006.01)

(52) U.S. Cl.
CPC ............ *C07D 217/04* (2013.01); *A61K 31/472* (2013.01); *A61K 45/06* (2013.01)

(58) Field of Classification Search
None
See application file for complete search history.

(56) References Cited

FOREIGN PATENT DOCUMENTS

EP    0956865 A1 * 11/1999

OTHER PUBLICATIONS

Soerensen et al, BMC Musculoskeletal Disorders (2010), 11, No. 250, pp. 1471-1474.*
International Search Report for PCT/EP 2013/059207 dated Jul. 10, 2013.*

* cited by examiner

*Primary Examiner* — Zinna Northington Davis
(74) *Attorney, Agent, or Firm* — Merchant & Gould P.C.

(57) ABSTRACT

There is provided compounds for treating bone loss diseases and for preventing bone loss. Specifically the present invention relates to compounds, preferable isoquinolene derivatives.

9 Claims, 9 Drawing Sheets

A

B

ANABOLIC COMPOUNDS FOR TREATING AND PREVENTING BONE LOSS DISEASES

This application is a National Stage Application of PCT/EP2013/059207, filed 3 May 2013, which claims benefit of Serial No. PA 2012 00320, filed 8 May 2012 in Denmark, and which claims benefit of U.S. Provisional Ser. No. 61/644,046, filed 8 May 2012 and which applications are incorporated herein by reference. To the extent appropriate, a claim of priority is made to each of the above disclosed applications.

FIELD OF THE INVENTION

The present invention relates to anabolic compounds for treating bone loss diseases and for preventing bone loss. Specifically the present invention relates to isoquinolene derivatives for use in such treatment.

BACKGROUND OF THE INVENTION

Bone is a dynamic organ that turns over continually through bone resorption and bone formation. This remodeling process functions to maintain calcium balance, repair bone damaged from mechanical stresses, adjust for changes in mechanical load, and remove old bone material that has degraded with age. Bone mass is regulated by a delicate balance between bone resorption mediated by osteoclasts and bone formation mediated by osteoblasts.

Osteoblasts are cells of mesenchymal origin and synthesize the precursors that form the organic extracellular matrix, also called the osteoid or ground substance, which are composed mainly of type I collagen and various non-collagen proteins such as osteocalcin, osteopontin, osteonectin, proteoglycans, and alkaline phosphatases. Once a layer of organic matrix is laid down by the osteoblasts, mineralization occurs through deposition of hydroxyapatite along and within the organic matrix. Osteocalcin, a protein produced by the osteoblasts, binds and concentrates the calcium in the matrix. Consecutive layers of organic matrix added by the osteoblasts through cycles of osteoid secretion and mineralization (appositional growth) form sheets or rings of mineralized matrix, which fuse together to form a lattice structure of connected bone. A proportion of osteoblasts becomes trapped as osteocytes in the lacunae, which is connected by a system of canaliculi. In some conditions, such as in the fetus and certain bone disorders, the organic matrix is arranged in a weave-like form and results in a type of bone referred to as woven, immature, or primitive bone. Changes to stiffness of bone occurs by modulating the level of hydroxyapatite in the matrix, with higher mineral content providing stiffness and rigidity and a lower mineral content providing bone flexibility.

Osteoclasts, the primary cells responsible for bone resorption, arise from hematopoietic cells of the macrophage/monocyte lineage and are multinucleated cells {i.e., polykaryons) that form by fusion of monocytes. Osteoclasts secrete various enzymes that act in dissolution of bone material. For example, tartrate resistant acid phosphatase (TRACP) decalcifies the bone while cathepsin K digests the bone matrix proteins. Osteoclasts also acidify the surrounding environment through vacuolar H+-ATPase activity, thereby further promoting bone resorption.

The development and function of osteoclasts are tightly coupled to the activity of osteoblasts, which secrete cellular factors affecting osteoclast differentiation and activity. The osteoblast protein RANKL (receptor for activating NFkB ligand) is a key regulator that stimulates differentiation of osteoclast precursor cells and activates mature osteoclasts. Osteoblasts also produce a decoy ligand, osteoprotegrin (OPG), which competes with RANKL and inhibits its activity. Expression of RANKL is regulated by cytokines (e.g., IL-I, IL-6, IL-11 and TNF-alpha), glucocorticoids, and parathyroid hormone (PTH). The presence of RANKL upregulators leads to enhanced bone resorption and a corresponding loss of bone mass. OPG production is upregulated by cytokines IL-I and TNF-alpha, steroid hormone beta-estradiol, and mechanical stress, thereby stimulating bone formation. In contrast, glucocorticoids, and prostaglandins suppress production of OPG and thus enhance bone resorption. This intricate interaction between the osteoblasts and osteoclasts provides a mechanism for adapting to conditions requiring additional bone mass (e.g., increased mechanical load) as well as maintenance of bone mass.

Current treatments for bone loss diseases include antiresorptive agents such as bisphosphonates, calcitonin, estrogen, and vitamin D supplementation, which limit bone resorption and prevent loss of bone mass. Anabolic agents that promote bone formation have also been studied, with PTH peptide teriparatide being the only FDA approved anabolic agent. Thus there is a need for development of novel anabolic drugs to be used for treatment of bone loss diseases and/or prevention of bone loss. Moreover, therapies specifically directed against the cellular basis of bone metabolism and remodeling may avoid some of the undesirable side effects associated with some current treatments.

The abnormal regulation of osteoclast and osteoblast activities can lead to various bone disorders. The clinical presentations of decreased bone formation and/or increased bone resorption include loss of bone mass and/or decrease in structural integrity of the bone matrix. Both conditions can lead to an increased risk of bone fractures. The most common form of bone loss, primary osteoporosis, is a significant health problem because nearly 5 to 20% of the human female population suffers from the condition. Although not as prevalent as in the female population, age-related osteoporosis also affects a significant percentage of males.

Bone possesses the intrinsic capacity for regeneration as part of the repair process in response to injury. However, there are cases of fracture in which bone regeneration is impaired. For example up to 13% of fractures that occur in the tibia are associated with delayed healing or non-healing fractures. There are currently a number of treatment methods available which can be used either alone or in combination, for management of these complex clinical situations.

The tissue-engineering approach is a promising strategy added in the field of bone regenerative medicine which aims to generate new, cell-driven, functional tissues. In essence, bone-tissue engineering combines progenitor cells, such as human Mesenchymal Stem Cells (hMSC) or mature cells (for osteogenesis) seeded in biocompatible scaffolds and ideally in three-dimensional tissue-like structures (for osteoconduction and vascular ingrowth), with appropriate growth factors (for osteoinduction), in order to generate and maintain bone. The need for such improved composite grafts is obvious, especially for the management of large bone defects, for which the requirements for grafting material are substantial. One of the main disadvantages of tissue-engineering approaches is their substantial cost, mainly due to use of recombinant proteins (Growth factors like Bone Morphogenetic Proteins). Therefore identification of molecules that can enhance bone formation is highly desirable.

EP 0956865 A1 discloses numerous Rho kinase inhibitors that have various therapeutic effects. In Exp. Example 8 some of the compounds have shown to have inhibitory action on bone resorption in vitro. Meanwhile, none of these tested compounds share the chemical structure of the compounds of the present invention. EP 0956865 A1 has a general formula (II), which encompasses the compounds of the present invention. According to the description in EP 0956865 A1 the compounds of formula (II) can be used to treat hypertension, angina pectoris, cerebrovascular contraction, asthma, inflammation and, brain function disorder, eripheral circulation disorder, arteriosclerosis, cancer, autoimmune diseases, AIDS, osteoporosis, retinopathy, immature birth, and digestive tract infections. However, there is no specific teaching in EP 0956865 A1 that the claimed compounds of the present invention would be good enhancers of bone formation.

Soerensen et al (BMC Muscular Disorders, 2010, vol 11, no 250, pp 1471-1474) disclose tests of kinase inhibitors in osteoclast and there effect on bone resorption. One of the inhibitors tested is H-8 (table 1) that falls under the claimed subject-matter of the present invention. Meanwhile, according to table 1 in Soerensen et al H-8 has no effect on osteoclastic acid secretion. Thus, Soerensen et al teaches away from the present invention.

SUMMARY OF THE INVENTION

The present disclosure provides specific isoquinolene derivatives that have shown particularly useful in the treatment of bone loss diseases.

The present invention provides a compound represented by the formula (I) for use in treating a degenerative bone disorder:

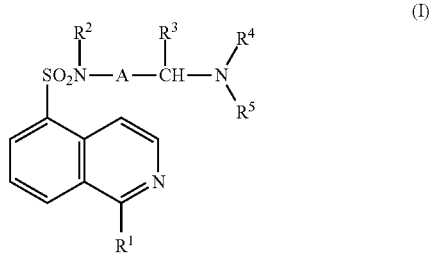

wherein
$R^1$ is selected from the group consisting of a hydrogen atom, a chlorine atom and a hydroxyl group;
$R^2$ is selected from the group consisting of hydrogen, an alkyl group having 1 to 8 carbon atoms and a benzyl group, or directly bonded with $R^3$ to form Z;
$R^3$ is selected from the group consisting of a hydrogen atom and an alkyl group having 1 to 8 carbon atoms, or directly bonded with $R^2$ to form Z;
said Z being selected from the group consisting of an unsubstituted ethylene group, an ethylene group substituted with an alkyl group having 1 to 8 carbon atoms, an unsubstituted trimethylene group, and a trimethylene group substituted with an alkyl group having 1 to 8 carbon atoms;
provided that where $R^2$ and $R^3$ are not directly bonded with each other, $R^1$ is a hydrogen atom, and where $R^2$ and $R^3$ are directly bonded with each other to form Z, $R^1$ is selected from the group consisting of a hydrogen atom, a chlorine atom and a hydroxyl group;
$R^4$ and $R^5$ are independently selected from the group consisting of a hydrogen atom, an alkyl group having 1 to 6 carbon atoms which is unsubstituted or substituted with a phenyl group, and a phenyl group, or $R^4$ and $R^5$ are each alkylene groups having 1 to 5 carbon atoms and bonded with each other directly or through an oxygen atom to form a heterocyclic ring in cooperation with the adjacent nitrogen atom, the total number of carbon atoms in the two alkylene groups not exceeding 6; and
A is an alkylene group having 1 to 5 carbon atoms which is unsubstituted or substituted with an alkyl group having 1 to 8 carbon atoms;
or a pharmacologically acceptable acid salt thereof.

Preferred compounds of the present invention are those of formula (I), wherein $R^1$ is a hydrogen atom; $R^2$ is selected from the group consisting of hydrogen, an alkyl group having 1 to 8 carbon atoms and a benzyl group; $R^3$ is selected from the group consisting of a hydrogen atom and an alkyl group having 1 to 8 carbon atoms; and A is an alkylene group having 1 to 5 carbon atoms, which is unsubstituted or substituted with an alkyl group having 1 to 4 carbon atoms.

More preferred compounds of the present invention are those of formula (I), wherein $R^3$, $R^4$ and $R^5$ are each hydrogen atoms; and A is an alkylene group having 1 to 5 carbon atoms.

Most preferred compounds of the present invention are those of formula (I), wherein, wherein A is a methylene group. A particularly preferred compound is N-[2-(methylamino)ethyl]-5-isoquinolinesulfonamide, especially its dihydrochloride salt.

The compounds of the present invention are very potent in the treatment of bone loss diseases, such as osteoporosis, optionally selected from postmenopausal osteoporosis, senile osteoporosis, and juvenile osteoporosis. The compounds are also potent in the treatment of a degenerative bone disorders associated with an endocrinopathy, such as hypercorticolism, hypogonadism, hyperparathyroidism, and hypoparathyroidism. The degenerative bone disorder may also be osteodystrophy; osteopenia or a degenerative bone disorder caused by an imbalance of osteoclast and osteoblast activity that results in net excess of bone resorption over bone formation.

The acid salts of the isoquinoline derivatives of formula (I) are pharmacologically acceptable non-toxic salts. As examples of the acid, there may be mentioned such inorganic acids as hydrochloric acid (e.g. dihydrochloride), hydrobromic acid, phosphoric acid and sulfuric acid and such organic acids as acetic acid, citric acid, tartaric acid, lactic acid, succinic acid, fumaric acid, maleic acid, and methanesulfonic acid.

Generally, the uses comprise administering to a subject afflicted with a bone loss disease an amount of an isoquinolene derivative effective to treat the disorder. The inhibitor compounds can reduce bone loss and/or increase bone formation to reduce fracture risk in the afflicted subject. Bone degenerative disorders that can be treated with the compounds include, among others, various forms of osteoporosis (e.g., postmenopausal osteoporosis, senile osteoporosis, juvenile osteoporosis). Other bone loss diseases that can be treated with the compounds of the present invention include those associated with abnormal secretion of a hormone (i.e., endocrinopathy) that affects bone metabolism. Exemplary hormones influencing bone metabolism include androgens (e.g., testosterone), estrogen, parathyroid hormone, calcitriol, and calcitonin. Endocrinopathies that result in bone degeneration include, among others, hypereorticolism, hypogandism, cancer induced bone loss, and hypoparathyroidism.

In some embodiments, the compounds can be used to treat bone degenerative disorders associated with a genetic abnormality. The genetic abnormality may affect osteoclast activity, osteoblast activity, or a combination of osteoclast and osteoblast function such that there is an imbalance of bone resorption over bone formation. In some genetic abnormalities, there is excessive bone remodelling that produces a structurally compromised bone structure, resulting in an increased probability of fracture. Compounds can be used to attenuate the increased bone resorption present in many of these disorders, and where appropriate, increase bone mass sufficiently to decrease the fracture risk. Examples of genetic disorders characterized by bone degeneration include osteogenesis imperfecta, homocystinuria, gonadal dysgenesis, and hypophosphatasia.

In other aspects, the compounds of the present invention can be used as prophylaxis for reducing or preventing bone loss and thereby reduce the risk of fractures. The inhibitory compounds can be administered to subjects having a risk factor associated with bone loss. These factors can be gender (e.g., females) or age-related. Other risk factors are associated with low calcium intake in the diet, tobacco use, sedentary lifestyle, family history, and genetic background.

Suitable for the treatment according to the present invention are all of the mentioned isoquinolene derivatives, such as H-8, and various derivatives thereof. These include, where applicable, the salts, hydrates, and solvates.

In some embodiments, the isoquinolene derivatives can be in the form of prodrugs, in which one or more of the available primary or secondary amine groups are masked with a pro-group.

The compounds can be used alone or in combination with bone modulating agents that reduce the level of bone loss (i.e., antiresorptive) or increase bone formation (i.e., osteo-anabolic). Antiresorptive agents attenuate or inhibit bone resorption and include agents such as 1,25 dihydroxyvitamin D3, bisphosphonates, calcitonin, and estrogen. Osteo-anabolic agents promote bone formation and include agents such as parathyroid hormone, parathyroid hormone analogs, androgens, fluoride, strontium, vitamin K2, and growth hormone. The bone modulating agents can be administered adjunctively as a composition, or administered separately or sequentially, in combination with the compounds.

DETAILED DESCRIPTION THE INVENTION

Definitions

Figure 1:
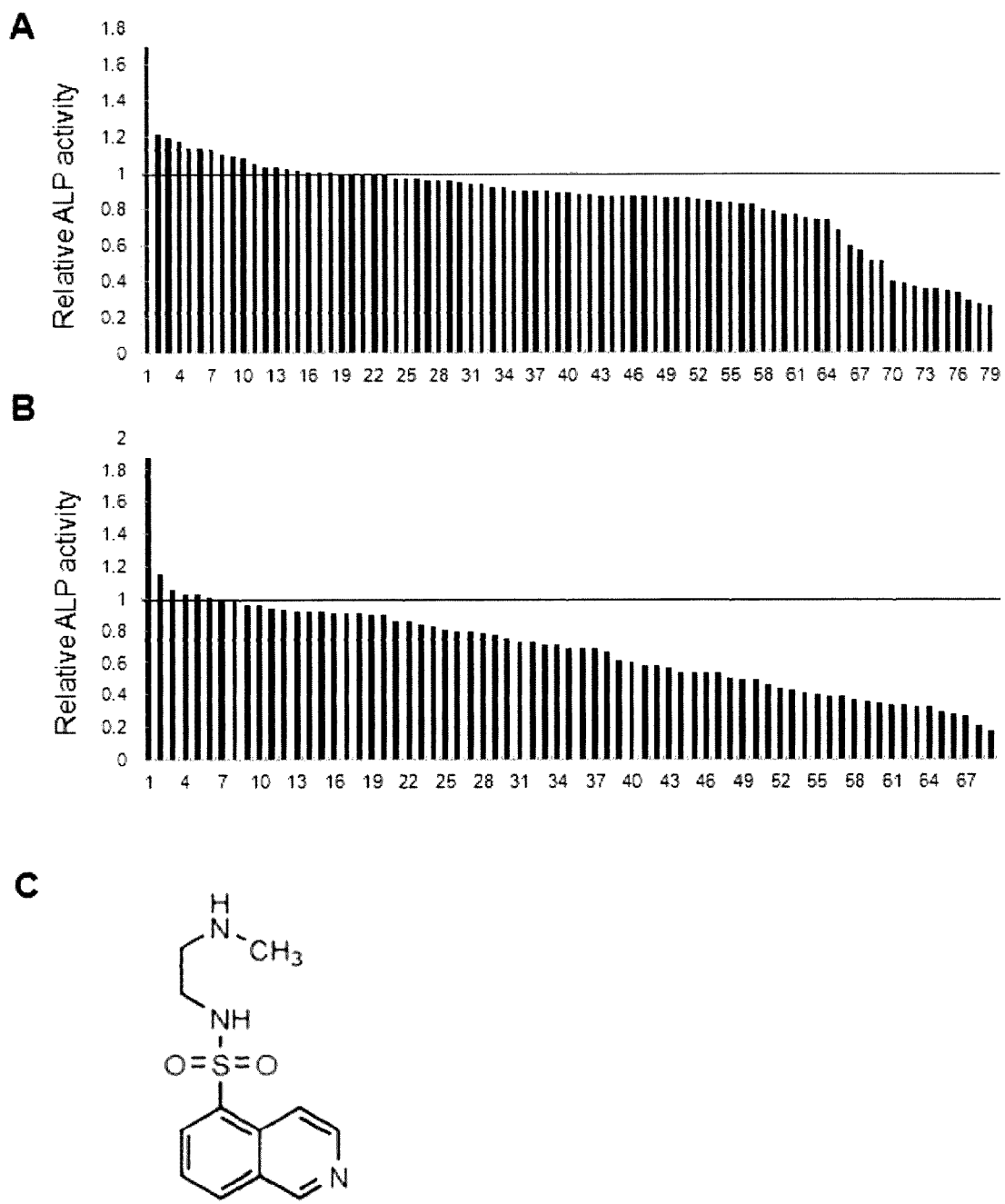
FIG. 1 shows that screening of the small molecule kinase inhibitor library identified H-8 as a potent stimulator of ALP activity. hMSC-TERT cell line was used for the screening and each kinase inhibitor was added individually to the osteogenic inducing media (OIM) at 1 µM (A) and 10 µM (B) concentrations. Quantification of ALP activity 6 days after induction of differentiation revealed that H-8 enhances ALP activity significantly at both concentrations. (C) Shows the chemical structure of H-8.

The terms used in the description herein will have their ordinary and common meaning as understood by those skilled in the art, unless specifically defined otherwise. As used throughout the instant application, the following terms shall have the following meanings:

"Bone formation" and "bone deposition" refers to the process of laying down of new bone material. The osteoblast is the primary cell responsible for forming the bone organic matrix and incorporation of hydroxyapatite crystals during mineralization of the matrix. As such, bone formation encompasses the synthesis of the organic matrix and the mineralization process involving incorporation of hydroxyapatite.

"Bone resorption" refers to the process of bone removal or dissolution. The osteoclast is the primary cell responsible for dissolution of the bone matrix.

"Bone loss disease" refers to a disease or condition characterized by a decrease in bone mass and/or an increase in probability of fractures because of compromised structural integrity of the bone. Many bone loss diseases arise from an imbalance between bone formation and bone resorption. This imbalance can be caused by a reduction in osteoblast mediated bone formation, an increase in osteoclast mediated bone resorption, or a combination of changes to osteoblast and osteoclast activity.

"Endocrinopathy" refers to a disease or condition of abnormal secretion of a hormone. Abnormal is meant an increase or decrease in levels of a specified hormone that can give rise to a medical condition. An endocrinopathy is not limited to dysfunction of an endocrine gland but applies to an abnormality in the secretion of a hormone by any cell or organ.

"Estrogen deficiency" refers to a decrease in estrogen levels that is capable of leading to a medical condition associated with the low estrogen levels, but which may or may not have actually resulted in clinical or other diagnostic presentation of the condition.

"Menopause" and "menopausal" refers to the stage of the human female reproductive cycle that occurs as the ovaries decrease estrogen and progesterone production, causing the reproductive system to gradually stop menstruating. The menopausal period can last anywhere from about 6 months to about 8 years. The average onset of menopause is about 50.5 years, but some women enter menopause at a younger or later age. Premature menopause, also called Premature Ovarian Failure, is menopause occurring before the age of 40, and can be characterized by abnormally low levels of estrogen and high levels of FSH in the affected subject. Postmenopausal refers to the period following menopause. Induced menopause occurs when the ovaries are surgically removed {e.g., by bilateral oophorectomy) or are damaged by radiation or drugs. Perimenopause refers to the menopause transition that begins about 6 years before the natural menopause when the levels of hormones produced by the aging ovaries fluctuate leading to irregular menstrual patterns.

"Osteo-anabolic agent" refers to a compound or composition that induces or promotes bone formation. Generally, the primary target of an osteo-anabolic agent is the osteoblast, the cell responsible for deposition of bone, or the cells that gives rise to osteoblasts, such as mesenchymal stem cells. However, osteo-anabolic agents can also include compounds and compositions that alter the substances or cellular products involved in bone formation, such as osteocalcin involved in binding to hydroxyapatite.

"Osteopenia" refers to a decrease in bone mineral density that is not as severe as osteoporosis. Osteopenia is indicated where there is a decrease in bone mineral density, whether or not osteoporosis is present, as detected by a suitable diagnostic procedure, such as a radiographic technique. The WHO defines osteopenia as a bone density between 1 standard deviation and 2.5 standard deviations below the bone density of a reference standard (i.e., generally a healthy young adult of about 30 years old).

"Osteoporosis" refers to a degenerative bone disorder characterized by low bone mass and microarchitectural deterioration of bone tissue, leading to enhanced bone fragility and increased fracture risk. Primary osteoporosis represents bone mass loss unassociated with any other illness and is typically related to aging and age-related loss of gonadal function. Forms of primary osteoporosis are postemenopausal osteoporosis and senile osteoporosis. Primary osteoporosis also includes idiopathic osteoporosis, which is osteoporosis where an underlying or secondary cause of the bone degeneration is unknown. Secondary osteoporosis refers to osteoporosis resulting from another condition or illness besides the age-related bone degeneration encompassed by primary osteoporosis. The WHO defines osteoporosis as bone density 2.5 standard deviations below the bone density of a reference standard (i.e., generally a healthy young adult of about 30 years old).

Treatment of Bone Loss Diseases

Bone remodeling is a complex process involving bone resorption by osteoclasts and bone formation by osteoblasts. To grow or maintain bone mass, there must be an appropriate balance in the rates of bone formation and bone resorption. Any abnormal imbalance between the two processes, such as excessive bone remodeling or a net excess of bone resorption over bone formation, can lead to weaknesses in bone structure and a corresponding increased risk of fractures. The present disclosure provides compounds for treating these bone loss diseases as well as prophylactic approaches for preventing bone loss that can lead to increased fracture risk. These treatments are based on the use of compounds to enhance osteoblastic differentiation of human mesenchymal stem cells (hMSC) thereby decreasing the excessive bone loss associated with abnormal activity of osteoclasts. For the purposes disclosed herein, the compounds can be used independently or in combination with other modulators of bone remodeling (i.e., antiresorptive agents and osteo-anabolic agents), for treatment as well as prophylaxis. Thus, the compounds can be used in the preparation of various medicaments for the treatment of bone loss diseases.

In the present disclosure, various bone loss diseases can be treated by administering to a subject in need thereof an amount of a compounds compound effective to treat the degenerative bone disorder. The diagnosis of a particular disorder can be based on clinical presentations typically used by those skilled in the art to diagnose the disorder. As further discussed herein, other diagnostic criteria such as the presence of biochemical and molecular markers of the disease, can be used independently or as a supplement to the examination of the clinical presentations.

Accordingly, in some embodiments, the compounds can be used to treat primary osteoporosis, which is a loss of bone mass unrelated to any other underlying disease or illness. In other words, the loss of bone mass is not caused by another condition, such as hormonal imbalances resulting from a pathological condition or other diseases that indirectly affect bone metabolism. Two general types of primary osteoporosis are described in the art. Type I, also referred to as high turnover or postmenopausal osteoporosis, is correlated with a decrease in hormone levels secreted by the ovaries in the postmenopausal period. The exact etiology of the disease has not been completely resolved. The condition occurs in about 5 to 20% of the female population, and gives rise to an increased fracture risk. The disease affects females because they undergo a rapid loss of bone mass beginning at menopause and lasting for about 4 to about 8 years, followed by a more gradual bone loss later in life. Type II, also referred to as low turnover or senile osteoporosis, can arise when the processes of bone resorption and bone formation are not coordinated such that there is a net excess of bone resorption over bone formation. Whereas Type I osteoporosis occurs primarily in women, Type II osteoporosis can occur in women and men with equal frequency. Thus, some women can have both Type I and Type II osteoporosis.

Other forms of primary osteoporosis are idiopathic osteoporosis, an osteoporotic condition where there is no identifiable cause for the bone loss. Idiopathic osteoporosis can affect children and adults. Juvenile osteoporosis is osteoporosis occurring in children between the ages of about 8 and about 14 years of age. In juvenile osteoporosis, impairment of bone growth occurs over a period of several years, and in most cases, goes into remission. However, the period of impaired bone growth and remodeling can lead to skeletal deformations, such as curvature of the spine and short stature. Moreover, inadequate accumulation of bone mass could lead to an increased risk of fractures later in life.

In some embodiments, the compounds can be used to treat bone loss diseases arising from a secondary condition, where the bone degeneration is a consequence of the underlying medical condition or disease. In some embodiments, specifically excluded from the treatments herein is bone degeneration occurring because of dysregulation of immune system activity. These include autoimmune diseases that promote bone destruction and diseases that target organs indirectly affecting bone metabolism. Exemplary autoimmune diseases associated with bone destruction are rheumatoid arthritis and osteoarthritis. Rheumatoid arthritis is a chronic inflammatory disease involving the synovial membranes and atricular structures of the joints. Exemplary autoimmune diseases affecting organs involved in regulating bone metabolism are glomerulonephritis and membrane glomerulonephritis. Glomerulitis refers to a specific set of renal diseases in which an immunologic mechanism triggers inflammation and proliferation of glomerular tissue. Immune complexes deposited or formed in the glomeruli trigger a chronic inflammatory reaction leading to compromised kidney function. Because the kidney is the key organ for production of the active form of vitamin D, and is responsible for regulating calcium and phosphate levels in the blood, kidneys damage results in the inability to absorb intestinal calcium and a corresponding increase in parathyroid hormone level, which induces calcium mobilization from the bone. Similarly, membranous glomerulonephritis is an immune related disease in which immune complexes formed via binding of antibodies to glomerular basement membrane antigens activate a response of the complement system that acts on the glomerular epithelial cells. The complexes in turn stimulate release of proteases and oxidants that damage the capillary walls, comprising the integrity of the glomeruli.

Effective Dosages

The active compound(s), or compositions thereof, will generally be used in an amount effective to treat or prevent the particular disease being treated. The compound(s) can be administered therapeutically to achieve therapeutic benefit or prophylactically to achieve prophylactic benefit. By therapeutic benefit is meant eradication or amelioration of the underlying degenerative bone disorder being treated and/or eradication or amelioration of one or more of the symptoms associated with the underlying disorder such that the patient reports an improvement in condition, notwithstanding that the patient may still be afflicted with the underlying disorder. Therapeutic benefit also includes halting or slowing the progression of the disease, regardless of whether improvement is realized. For prophylactic administration, the active compound can be administered to a patient at risk of developing a disorder characterized by, caused by or associated with bone loss and/or compromised bone integrity.

The amount of inhibitor compound(s) administered will depend upon a variety of factors, including, for example, the particular indication being treated, the mode of administration, whether the desired benefit is prophylactic or therapeutic, the severity of the indication being treated and the age and weight of the patient, the bioavailability of the particular active compound, etc. Determination of an effective dosage is well within the capabilities of those skilled in the art.

Initial dosages can be estimated from in vivo data, such as in animal models. Dosage amounts will typically be in the range of from about 1 mg/kg/day to about 100 mg/kg/day, 200 mg/kg/day, 300 mg/kg/day, 400 mg/kg/day or 500 mg/kg/day, but can be higher or lower, depending upon, among other factors, the activity of the inhibitory compound, its bioavailability, the mode of administration and various factors discussed above. Dosage amount and interval can be adjusted individually to provide plasma levels of the active compound(s) which are sufficient to maintain therapeutic or prophylactic effect. In cases of local administration or selective uptake, such as local topical administration, the effective local concentration of active compound(s) can not be related to plasma concentration. Skilled artisans will be able to optimize effective dosages without undue experimentation.

The compound(s) can be administered once per day, a few or several times per day, or even multiple times per day, depending upon, among other things, the indication being treated and the judgment of the prescribing physician.

Preferably, the active compound(s) will provide therapeutic or prophylactic benefit without causing substantial toxicity. Toxicity of the active compound(s) can be determined using standard pharmaceutical procedures. The dose ratio between toxic and therapeutic (or prophylactic) effect is the therapeutic index. Active compound(s) that exhibit high therapeutic indices are preferred.

EXAMPLE

This invention will now be described in detail with reference to the following Example
Screening of the Small Molecule Kinase Inhibitor Library
Screening of Kinase Inhibitor Library Identified H-8 as a Potent Stimulator of ALP Activity To identify novel molecules that can enhance osteoblast differentiation of hMSC, the present inventors screened a commercially available library of small molecule protein kinase inhibitors (Screen-Well™ Kinase Inhibitor Library, Biomol International®). This library contains 80 known kinase inhibitors of well-defined activity and covers a wide spectrum of signaling pathways. As a model for hMSC, the present inventors employed a a telomerized human mesenchymal stem cell line (hMSC-TERT). Each kinase inhibitor was added to the osteogenic inducing media (OIM) at 1 and 10 µM concentrations and ALP activity was determined 6 days after induction of differentiation. Several kinas inhibitors regulated ALP activity (FIG. 1) and among those, H-8 (N-[2-(methylamino)ethyl]-5-isoquinolinesulfonamide) enhanced ALP activity significantly at both concentrations. Names of the kinase inhibitors and their corresponding relative ALP activity are listed in tables 1 & 2.

H-8 (N-[2-(methylamino)ethyl]-5-isoquinolinesulfonamide) is an ATP-competitive protein kinase inhibitor that inhibits protein kinase A (PKA) and protein kinase G (PKG) selectively over protein kinase C(PKC) and Myosin Light Chain Kinase (MLCK) ($IC_{50}$'s=1.2 µM, 0.48 µM, 15 µM and 68 µM respectively). The chemical structure of H-8 is shown in FIG. 1C. Since effect of H-8 on osteoblastogenesis has not been studied before, the present inventors decided to further evaluate the effect of H-8 on in vitro osteoblast differentiation of hMSC and in vivo bone formation.

TABLE 1

Results of kinase inhibitor library screening at 1 µM concentration.

| NO. | Inhibitor name | Inhibitor target | Relative ALP activity |
|---|---|---|---|
| 1 | H-8 | PKA, C, G, MLCK | 1.700858 |
| 2 | Genistein, | Tyr Kinases | 1.214851 |
| 3 | Sphingosine | PKC | 1.194979 |
| 4 | Tyrphostin 46 | EGFRK, PDGFRK | 1.17935 |
| 5 | Olomoucine | CDK | 1.141668 |
| 6 | Daidzein | Ctrl- for Genistein | 1.139558 |
| 7 | N9-Isopropyl-olomoucine | CDK | 1.128065 |
| 8 | Tyrphostin AG 1478 | EGFRK | 1.096669 |
| 9 | H-7 | PKA, C, G, MLCK | 1.087305 |
| 10 | iso-Olomoucine | Ctrl - Olomoucine | 1.084084 |
| 11 | AG-370 | PDGFRK | 1.057463 |
| 12 | 5-Iodotubercidin | ERK2, ADK, CK1, CK2 | 1.03539 |
| 13 | ML-7 | MLCK | 1.03107 |
| 14 | HA-1077 | PKA, G | 1.020111 |
| 15 | 2-Aminopurine | P58 PITSLRE β1 | 1.016521 |
| 16 | Tyrphostin AG 1295 | Tyr Kinases | 1.007477 |
| 17 | Quercetin dihydrate | PI3K | 1.001259 |
| 18 | BML-259 | CDK5/P25 | 1.001155 |
| 19 | Palmitoyl-DL-carnitine Cl | PKC | 0.996619 |
| 20 | Tyrphostin 23 | EGFRK | 0.990362 |
| 21 | Roscovitine | CDK | 0.986536 |
| 22 | Y-27632 | ROCK | 0.984778 |
| 23 | ML-9 | MLCK | 0.982187 |
| 24 | DRB | CK-II | 0.971785 |
| 25 | HA-1004 | PKA, G | 0.97064 |
| 26 | AG-490 | JAK2 | 0.965735 |
| 27 | PP1 | Src Family | 0.962562 |
| 28 | KN-62 | CaMK II | 0.956047 |
| 29 | H-9 | PKA, C, G, MLCK | 0.95472 |
| 30 | ZM 449829 | JAK3 | 0.944425 |
| 31 | Tyrphostin 25 | EGFRK | 0.939668 |
| 32 | BAY 11-7082 | IKK pathway | 0.935629 |
| 33 | SC-514 | IKK2 | 0.923871 |
| 34 | Tyrphostin 1 | Ctrl- for Tyr kinase inhibitors | 0.921102 |
| 35 | AG-126 | IRAK | 0.905252 |
| 36 | Apigenin | CK-II | 0.902925 |
| 37 | Tyrphostin 47 | EGFRK | 0.901039 |
| 38 | Tyrphostin 51 | EGFRK | 0.899748 |
| 39 | H-89 | PKA | 0.892402 |
| 40 | Erbstatin analog | EGFRK | 0.889176 |
| 41 | HBDDE | PKC α, γ | 0.886057 |
| 42 | AG-494 | EGFRK, PDGFRK | 0.878764 |
| 43 | AG-825 | HER1-2 | 0.875367 |
| 44 | SU1498 | FLK1 | 0.871055 |
| 45 | Damnacanthal | P56 IcK | 0.871052 |
| 46 | HDBA | CaMK II | 0.870813 |
| 47 | ZM 336372 | cRAF | 0.869028 |
| 48 | Tyrphostin AG 1288 | Tyr kinases | 0.868386 |
| 49 | Lavendustin A | EGFRK | 0.864085 |
| 50 | HNMPA | IRK | 0.863987 |
| 51 | LY 294002, | PI3K | 0.862808 |
| 52 | Hypericin | PKC | 0.853373 |
| 53 | BML-257 | Akt | 0.844257 |
| 54 | RG-14620 | EGFRK | 0.830178 |
| 55 | Wortmannin | PI3K | 0.830079 |
| 56 | PP2 | Src Family | 0.827591 |
| 57 | SB-203580 | P38 MAPK | 0.823961 |
| 58 | GW 5074 | cRAF | 0.796888 |
| 59 | Piceatannol | Syk | 0.782984 |
| 60 | SB-202190 | P38 MAPK | 0.770809 |
| 61 | AG-1296 | PDGFRK | 0.768469 |
| 62 | SU 4312 | FLK1 | 0.748052 |
| 63 | LFM-A13 | BTK | 0.738079 |
| 64 | KN-93 | CaMk II | 0.734729 |
| 65 | AG-879 | NGFRK | 0.680057 |
| 66 | SP 600125 | JNK | 0.597787 |
| 67 | PD-98059 | MEK | 0.56168 |
| 68 | Rapamycin | mTOR | 0.509001 |
| 69 | Kenpaullone | GSK-3P | 0.504425 |
| 70 | BML-265 | EGFRK | 0.395361 |
| 71 | Rottlerin | PKC δ | 0.38736 |
| 72 | Ro 31-8220 | PKC | 0.360739 |
| 73 | Indirubin | GSK-3β, CDK5 | 0.357114 |
| 74 | GF 109203X | PKC | 0.353233 |
| 75 | U-0126 | MEK | 0.348526 |
| 76 | Tyrphostin9 | PDGFRK | 0.338845 |
| 77 | Triciribine | Akt signalling pathway | 0.289252 |
| 78 | Terreic acid | BTK | 0.272055 |
| 79 | Indirubin-3'-monoxime | GSK-3β | 0.258873 |
| 80 | Staurosporine | Pan specific | TOXIC |

TABLE 2

Results of kinase inhibitor library screening at 10 µM concentration.

| NO. | Inhibitor name | inhibitor target | Relative ALP activity |
|---|---|---|---|
| 1 | H-8 | PKA, C, G, MLCK | 1.869711 |
| 2 | AG-126 | IRAK | 1.155852 |
| 3 | AG-825 | HER1-2 | 1.056136 |
| 4 | Daidzein | Ctrl- for Genistein | 1.025069 |
| 5 | RG-1462 | EGFRK | 1.023578 |
| 6 | Tyrphostin 47 | EGFRK | 1.004945 |
| 7 | HDBA | CaMK II | 0.983558 |
| 8 | H-9 | PKA, C, G, MLCK | 0.978275 |
| 9 | Palmitoyl-DL-carnitine Cl | PKC | 0.961169 |
| 10 | ML-7 | MLCK | 0.956417 |
| 11 | HA-1004 | PKA, G | 0.942368 |
| 12 | Iso-Olomoucine | Ctrl - Olomoucine | 0.931808 |
| 13 | KN-62 | CaMK II | 0.922237 |
| 14 | Tyrphostin 1 | Ctrl- for Tyr kinase inhibitors | 0.921175 |
| 15 | LFM-A13 | BTK | 0.915398 |
| 16 | Wortmannin | PI3K | 0.912195 |
| 17 | HA-1077 | PKA, G | 0.908031 |
| 18 | Tyrphostin 46 | EGFRK, PDGFRK | 0.902881 |
| 19 | H-7 | PKA, C, G, MLCK | 0.901469 |
| 20 | ZM 449829 | JAK3 | 0.894551 |
| 21 | Tyrphostin 51 | EGFRK | 0.85661 |
| 22 | HNMPA | IRK | 0.855698 |

TABLE 2-continued

Results of kinase inhibitor library screening at 10 μM concentration.

| NO. | Inhibitor name | inhibitor target | Relative ALP activity |
|---|---|---|---|
| 23 | Quercetin dihydrate | PI3K | 0.835449 |
| 24 | Tyrphostin 25 | EGFRK | 0.823331 |
| 25 | Tyrphostin AG 1288 | Tyr kinases | 0.80202 |
| 26 | AG-370 | PDGFRK | 0.790212 |
| 27 | BML-257 | Akt | 0.788414 |
| 28 | SU1498 | FLK1 | 0.785328 |
| 29 | Genistein | Tyr Kinases | 0.76919 |
| 30 | AG-879 | NGFRK | 0.746717 |
| 31 | HBDDE | PKC α, γ | 0.729555 |
| 32 | BML-259 | CDK5/P25 | 0.725934 |
| 33 | Tyrphostin 23 | EGFRK | 0.706657 |
| 34 | Erbstatin analog | EGFRK | 0.702222 |
| 35 | ML-9 | MLCK | 0.68794 |
| 36 | 2-Aminopurine | P58 PITSLRE β1 | 0.685451 |
| 37 | KN-93 | CaMk II | 0.680214 |
| 38 | N9-Isopropyl-olomoucine | CDK | 0.666559 |
| 39 | Rapamycin | mTOR | 0.605748 |
| 40 | PD-98059 | MEK | 0.601679 |
| 41 | SC-514 | IKK2 | 0.579648 |
| 42 | GW 5074 | cRAF | 0.577256 |
| 43 | PP1 | Src Family | 0.566475 |
| 44 | Olomoucine | CDK | 0.540785 |
| 45 | AG-1296 | PDGFRK | 0.537555 |
| 46 | ZM 336372 | cRAF | 0.537278 |
| 47 | SU 4312 | FLK1 | 0.53487 |
| 48 | DRB | CK-II | 0.504335 |
| 49 | Lavendustin A | EGFRK | 0.493519 |
| 50 | Piceatannol | Syk | 0.4885 |
| 51 | SB-203580 | P38 MAPK | 0.457969 |
| 52 | LY 294002 | PI3K | 0.439045 |
| 53 | PP2 | Src Family | 0.426858 |
| 54 | Y-27632 | ROCK | 0.409213 |
| 55 | Apigenin | CK-II | 0.402695 |
| 56 | Roscovitine | CDK | 0.391753 |
| 57 | H-89 | PKA | 0.384745 |
| 58 | Indirubin-3'-monoxime | GSK-3β | 0.369675 |
| 59 | Tyrphostin AG 1295 | Tyr Kinases | 0.355597 |
| 60 | AG-490 | JAK2 | 0.348179 |
| 61 | Terreic acid | BTK | 0.337987 |
| 62 | AG-494 | EGFRK, PDGFRK | 0.329982 |
| 63 | Triciribine | Akt signalling pathway | 0.327766 |
| 64 | Damnacanthal | P56 IcK | 0.327279 |
| 65 | SP 600125 | JNK | 0.291344 |
| 66 | U-0126 | MEK | 0.281016 |
| 67 | SB-202190 | P38 MAPK | 0.270262 |
| 68 | Kenpaullone | GSK-3β | 0.205476 |
| 69 | Indirubin | GSK-3β, CDK5 | 0.179988 |
| 70 | 5-Iodotubercidin | ERK2, ADK, CK1, CK2 | Toxic |
| 71 | BAY 11-7082 | IKK pathway | Toxic |
| 72 | BML-265 | EGFRK | Toxic |
| 73 | GF 109203X | PKC | Toxic |
| 74 | Hypericin | PKC | Toxic |
| 75 | Ro 31-8220 | PKC | Toxic |
| 76 | Rottlerin | PKC δ | Toxic |
| 77 | Sphingosine | PKC | Toxic |
| 78 | Staurosporine | Pan specific | Toxic |
| 79 | Tyrphostin 9 | Tyr kinases | Toxic |
| 80 | Tyrphostin AG 1478 | PDGFRK | Toxic |

H-8 Enhances In Vitro Osteoblast Differentiation

Figure 2:
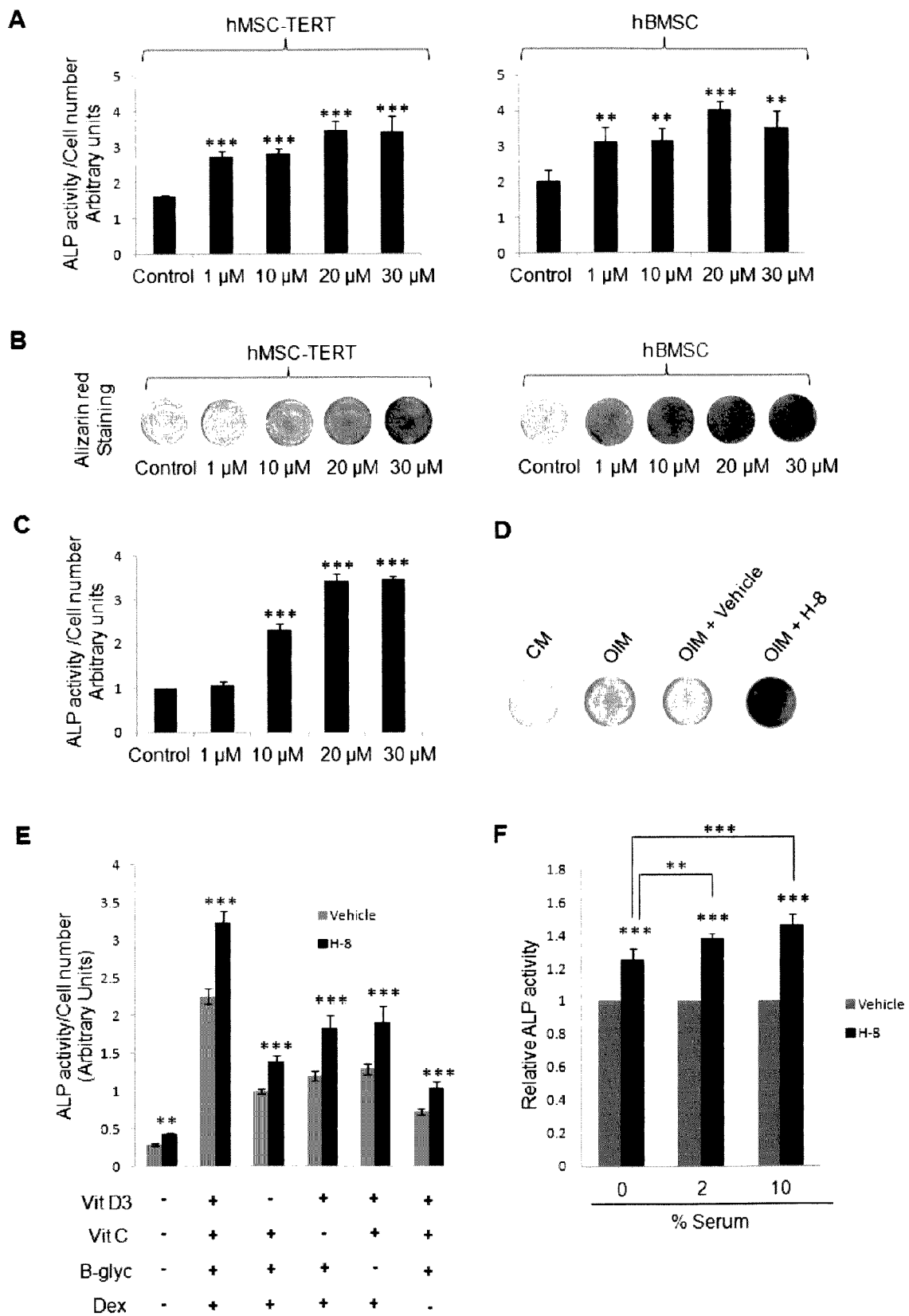
FIG. 2 shows the enhancing effect of H-8 on ALP activity and matrix mineralization of hMSC-TERT, Human Mesenchymal Stem Cell (hMSC), and Human adipose tissue derived MSC (hAT-MSC). A) Quantitation of ALP activity on day 6 of osteoblastic differentiation of hMSC-TERT and Human bone marrow derived MSC (hBMSC), showed a dose dependent enhancement of ALP activity, after H-8 treatment. B) Alizarin red staining on day 12 of osteoblastic differentiation of hMSC-TERT and hBMSC, showed that H-8 has a dose dependent enhancing effect on matrix mineralization. C) Quantitation of ALP activity on day 6 of osteoblastic differentiation showed that H-8 also has a dose dependent enhancing effect on ALP activity of hAT-MSC. D) Treatment of hAT-MSC with H-8 (25 µM) during osteoblast differentiation, enhanced matrix mineralization of the cells, as shown by alizarin red staining on day 10 of differentiation. E) Removing of osteoblastic differentiation inducers from the induction media showed that the enhancing effect of H-8 on ALP activity is not dependent on differentiation inducers. F) H-8 enhances ALP activity of hMSC, in the absence of serum. However, serum was found to have an additive effect on the H-8 induced ALP activity. $P \leq 0.05$, *$P \leq 0.005$ (significant difference with control cells).
Figure 3:
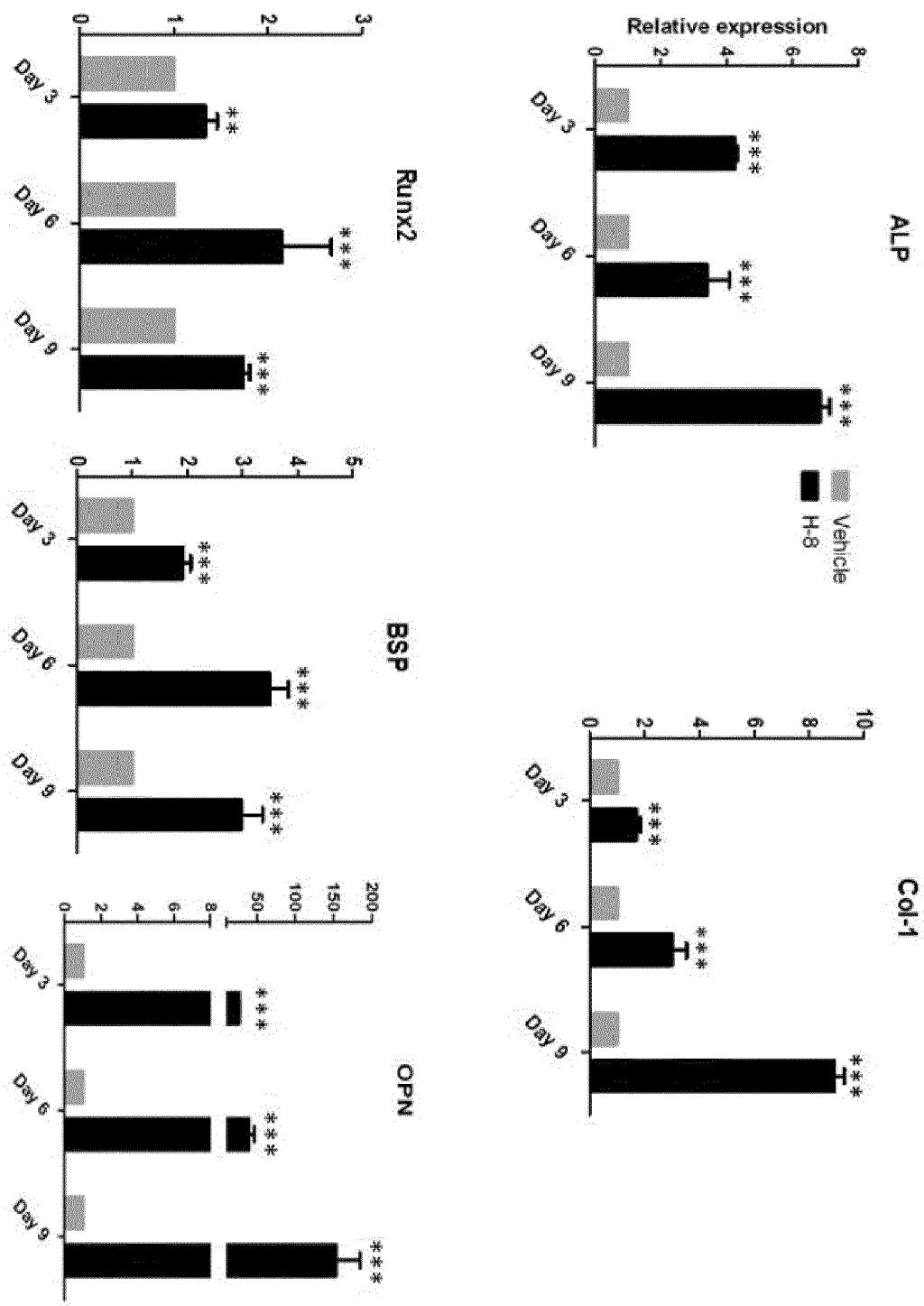
FIG. 3 shows the enhancing effect of H-8 on gene expression of osteoblastic markers. Adding H-8 (25 µM) to the osteogenic induction media, during 9-days in vitro hMSC osteogenic differentiation, enhanced expression of osteoblastic markers as shown by qRT-PCR analysis. $P \leq 0.05$, *$P \leq 0.005$ (significant difference as compared to vehicle).
Figure 4:
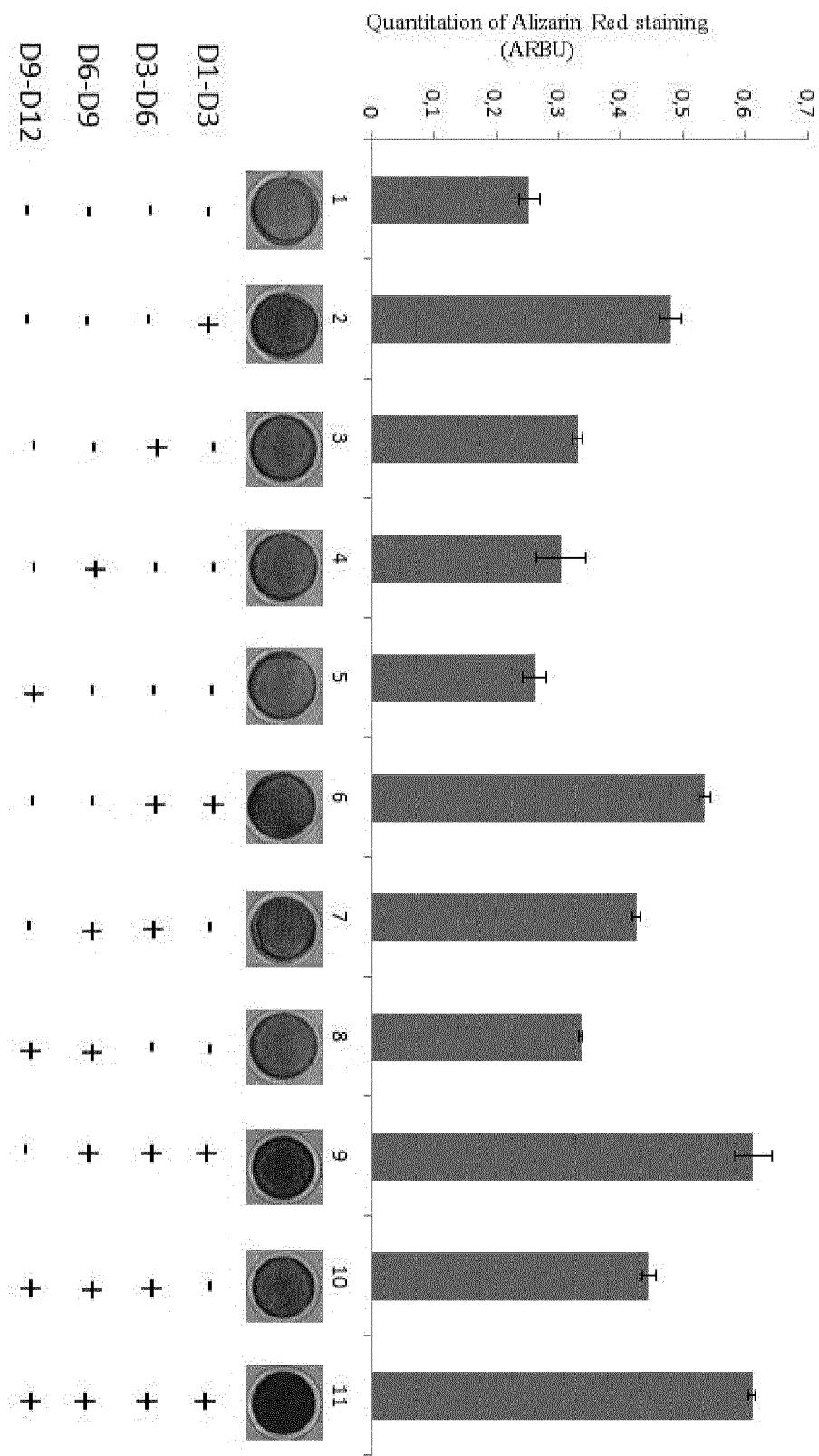
FIG. 4 shows stage specific effect of H-8 on in vitro matrix mineralization. H-8 was added (25 µM) to the OIM at different time points during 12-days period. Quantifying matrix mineralization as a marker of mature osteoblastic phenotype, revealed that H-8 is needed during the first 9 days to exert its effects on osteoblast maturation.

In order to confirm the results obtained from the initial screen, the present inventors incubated hMSC-TERT and primary human bone marrow derived MSC (hBMSC) in osteogenic induction medium (OIM) supplemented with H-8 (dose range 1-30 μM) or vehicle. H-8 treatment significantly increased ALP activity (FIG. 2A), and matrix mineralization, as shown by alizarin red staining (FIG. 2B), in a dose-dependent manner, in both hMSC-TERT and hBMSC. Similar effects were observed in human adipose tissue derived MSC (hAT-MSC) (FIGS. 2C & 2D). Furthermore, by removing each component of osteoblastic induction media, the present inventors showed that the enhancing effect of H-8 on ALP activity is not dependent on differentiation inducers (FIG. 2E). Moreover, by adding H-8 (25 μM) to the serum free induction media, the present inventors demonstrated that the enhancing effect of H-8 on ALP activity persists in the absence of serum. Moreover, the present inventors added serum to the induction media and thereby demonstrated an additive effect on H-8 induced ALP activity (FIG. 2F). In addition, H-8 enhanced gene expression of early and late osteogenic markers, as determined by qRT-PCR at different time points during 9-days in vitro hMSC osteogenic differentiation (FIG. 3). To determine the stage of differentiation at which the effect of H-8 was most apparent, the present inventors added H-8 (25 μM) to the OIM at different time points during 12-days period. Quantifying matrix mineralization as a marker of mature osteoblastic phenotype, revealed that H-8 is needed during the first 9 days to exert its effects (FIG. 4).

H-8 Treatment Enhances hMSC Survival in Vitro and in Vivo

Figure 5:
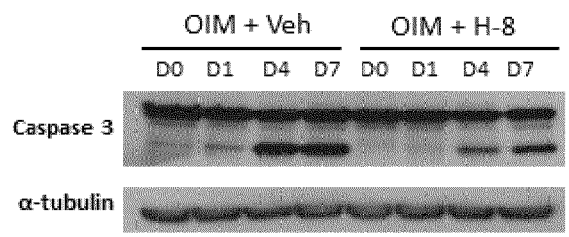
FIG. 5 shows H-8 treatment increased hMSC survival in vitro and in vivo. A) H-8 treatment of hMSC (25 µM) during osteoblast differentiation, decreased apoptosis, as shown by western blot analysis of activated Caspase-3. B) Luminescent imaging of vehicle/H-8 treated LUC2 expressing hMSC, implanted in the critical size mouse calvarial defect model showed that H-8 treatment enhances hMSC survival in vivo.
Figure 5:
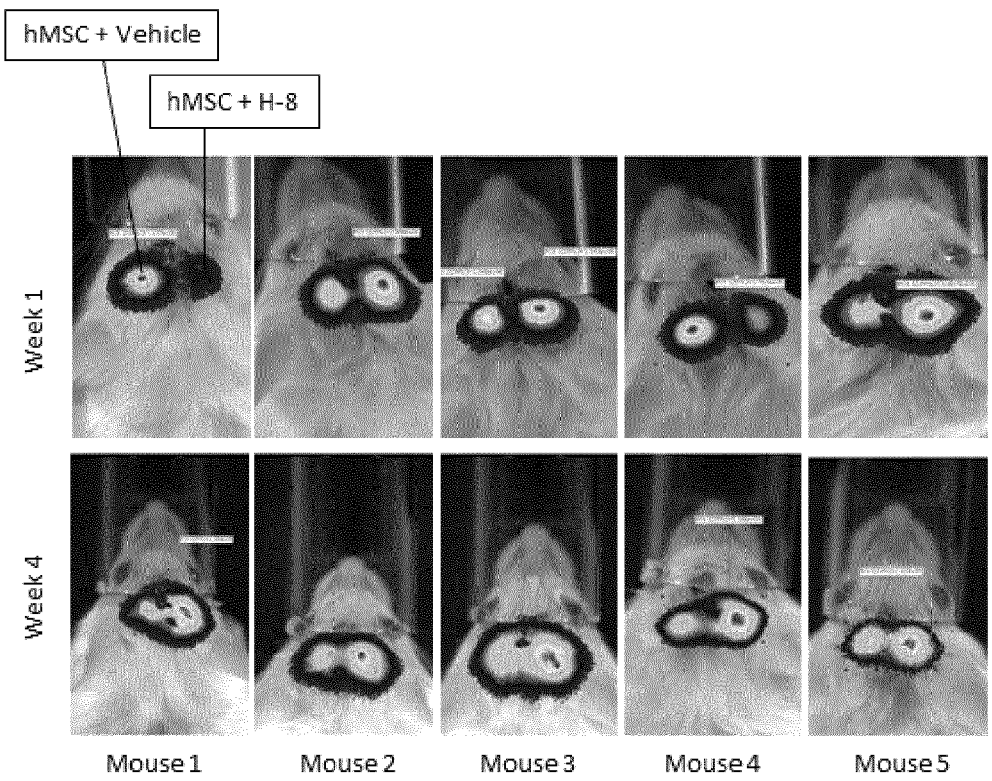

To investigate the effect of H-8 on hMSC survival in vitro, activation of Caspase-3 was evaluated, using western blot analysis. H-8 treatment was found to increase hMSC survival during osteoblast differentiation, as shown by reduced level of activated Caspase-3, (FIG. 5A). Moreover, H-8 increased hMSC survival in an in vivo bone regeneration model of mouse calvarial defect, 4 weeks after implantation of vehicle/H-8 treated hMSC (FIG. 5B).

H-8 Enhances In Vivo Heterotopic Bone Formation of hMSC

Figure 6:
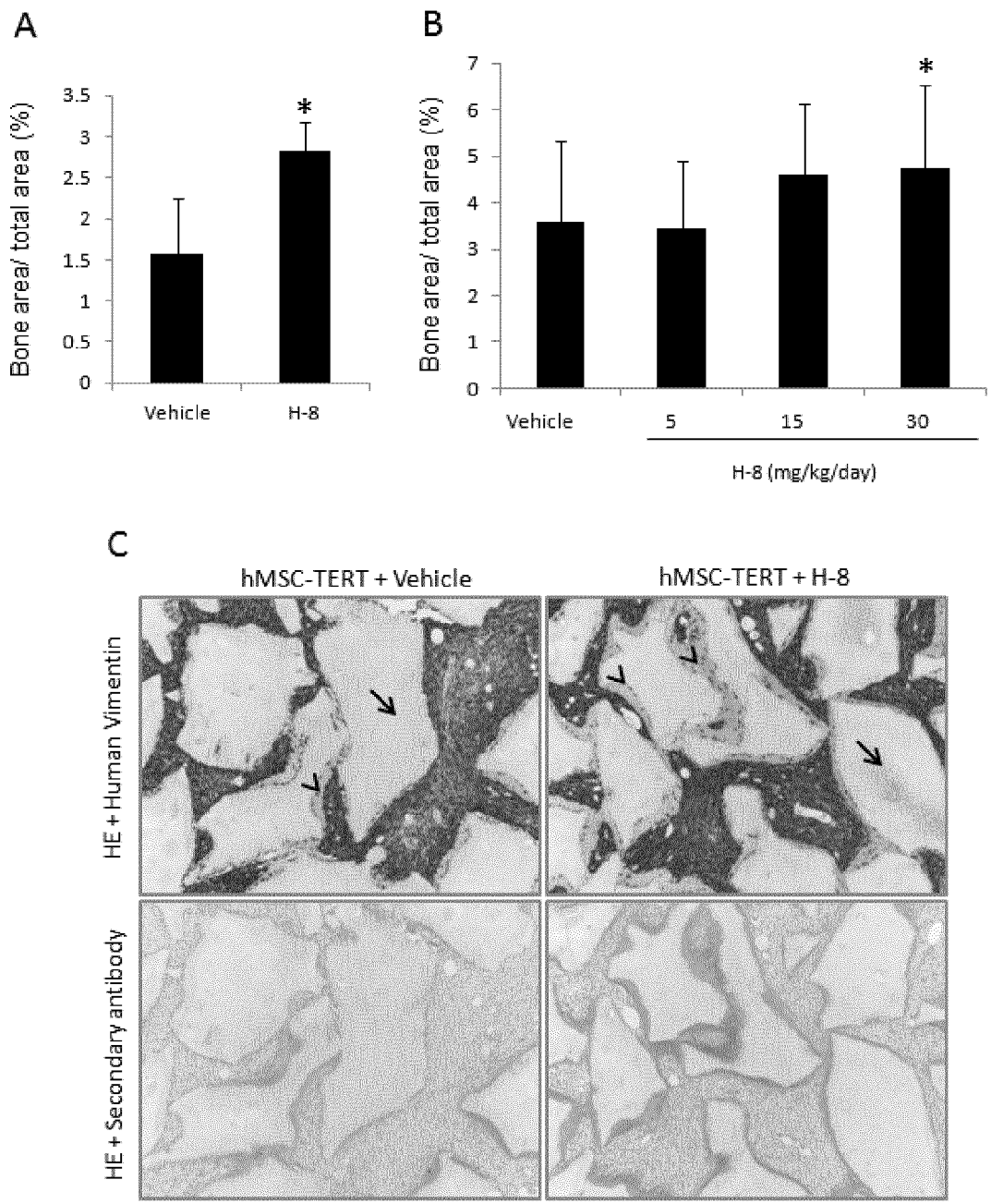
FIG. 6 shows that H-8 enhances in vivo heterotopic bone formation of hMSC. (A) Treatment of hMSC-TERT4 with H-8 (25 µM) for 7 days in vitro enhanced the in vivo heterotopic bone formation ability of the cells. (B) Systemic injection of H-8 at 30 mg/kg/day enhanced the amount of the heterotopic bone formed by hMSC-TERT4 implanted in SCID/NOD mice. (C) Human specific Vimentin staining confirmed that the newly formed heterotopic bone is of human origin. *$P \leq 0.05$ (significant difference as compared to vehicle).

To determine the effect of H-8 treatment on the ability of hMSC to form heterotopic bone in vivo, hMSC-TERT were treated with H-8 (25 μM) or vehicle for 7 days, mixed with hydroxyapatite/tricalcium phosphate (HA/TCP) as osteoconductive carrier, and implanted subcutaneously in SCID/NOD mice. Histological analysis of the implants after 8 weeks; revealed enhanced amount of heterotopic bone formation (FIG. 6A). In addition, increased amount of heterotopic bone formation was observed, when SCID/NOD mice received H-8 systematically (Intraperitoneally) at 30 mg/kg/day (For 4 weeks) following subcutaneous implantation of HA/TCP-hMSC-TERT (FIG. 6B). Human specific vimentin staining confirmed that the newly formed heterotopic bone is of human origin (FIG. 6C). In addition, Necropsy of the animals after systemic H-8 injection (5, 15, 30 mg/kg/day) for 4 weeks showed that all tissues looked normal and therefore systemic injection of H-8 have not had any toxic effects.

H-8 Treatment does not Affect Adipocyte Differentiation of hMSC

To determine the effect of H-8 on adipocyte differentiation of hMSC, H-8 was added (25 μM) to the adipogenic induction media (AIM) of hMSC-TERT. Measuring accumulation of lipid droplets, by quantification of the trapped Oil red O stain on day 15 of differentiation (FIG. 7A), and qRT-PCR analysis of adipogenic markers on day 10 of differentiation (FIG. 7B) demonstrated that H-8 does not affect adipocyte differentiation of hMSC.

Figure 7:
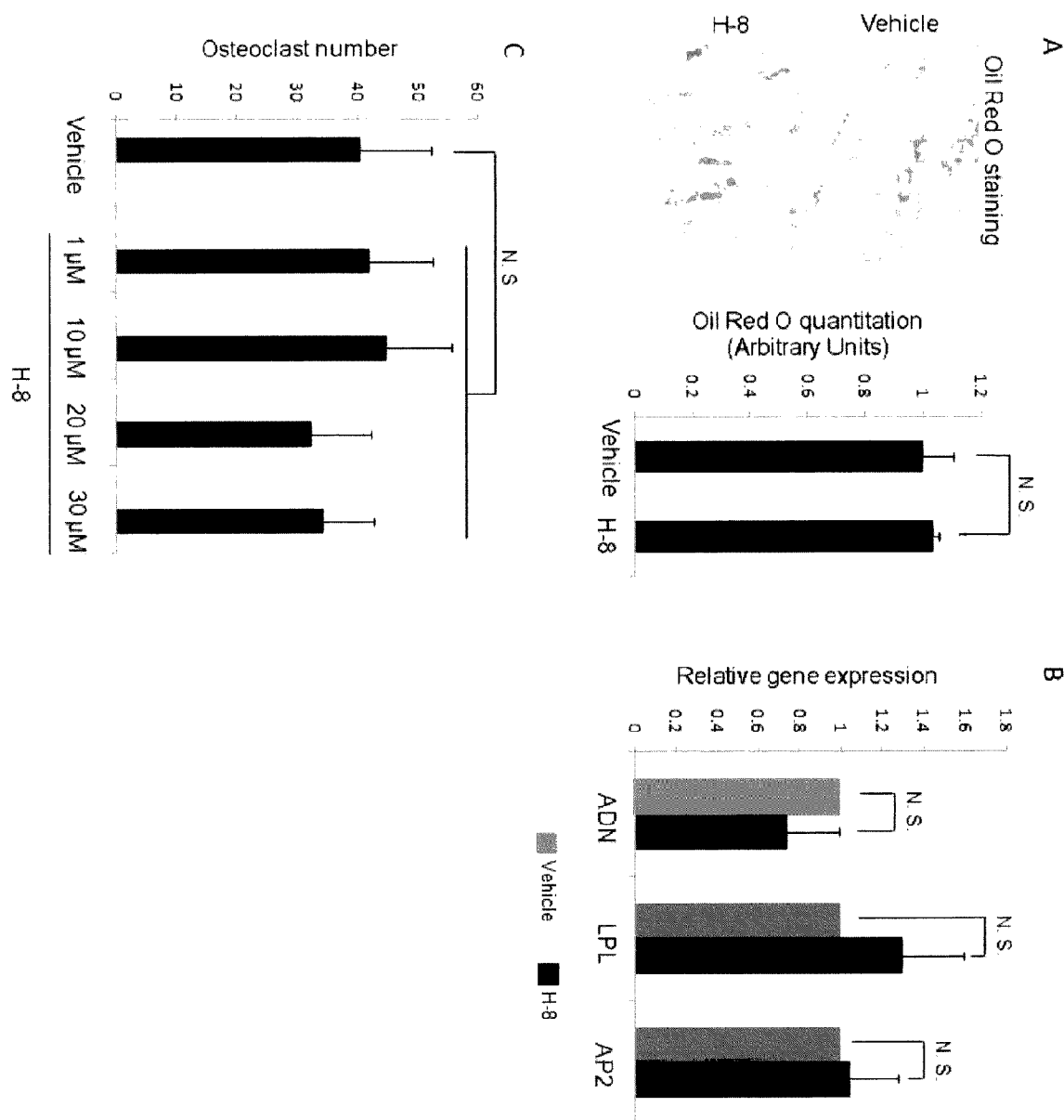
FIG. 7 shows that H-8 treatment does not affect adipocyte differentiation of hMSC or osteoclast differentiation of human CD14+ mononuclear cells. Quantitation of Oil red 0 staining on day 15 of differentiation (A) and qRT-PCR analysis of adipogenic markers on day 10 of adipogenic differentiation (B) showed that H-8 treatment does not affect differentiation of hMSC toward adipocytes. (C) Counting of TRAP positive multinucleated cells on day 5 of osteoclast differentiation of human CD14+ mononuclear cells showed that H-8 treatment does not affect osteoclast differentiation.

H-8 Treatment does not Affect Osteoclast Formation by Human CD14+ Mononuclear Cells The present inventors determined the effects of H-8 on osteoclast formation in peripheral blood-derived human CD14+ mononuclear cell cultures [139]. H-8 treatment (25 μM) did not affect osteoclast formation as determined by counting the number of tartrate-resistant acid phosphatase (TRAP)-positive multinucleated cells on day 5 of differentiation (FIG. 7C).

Figure 8:
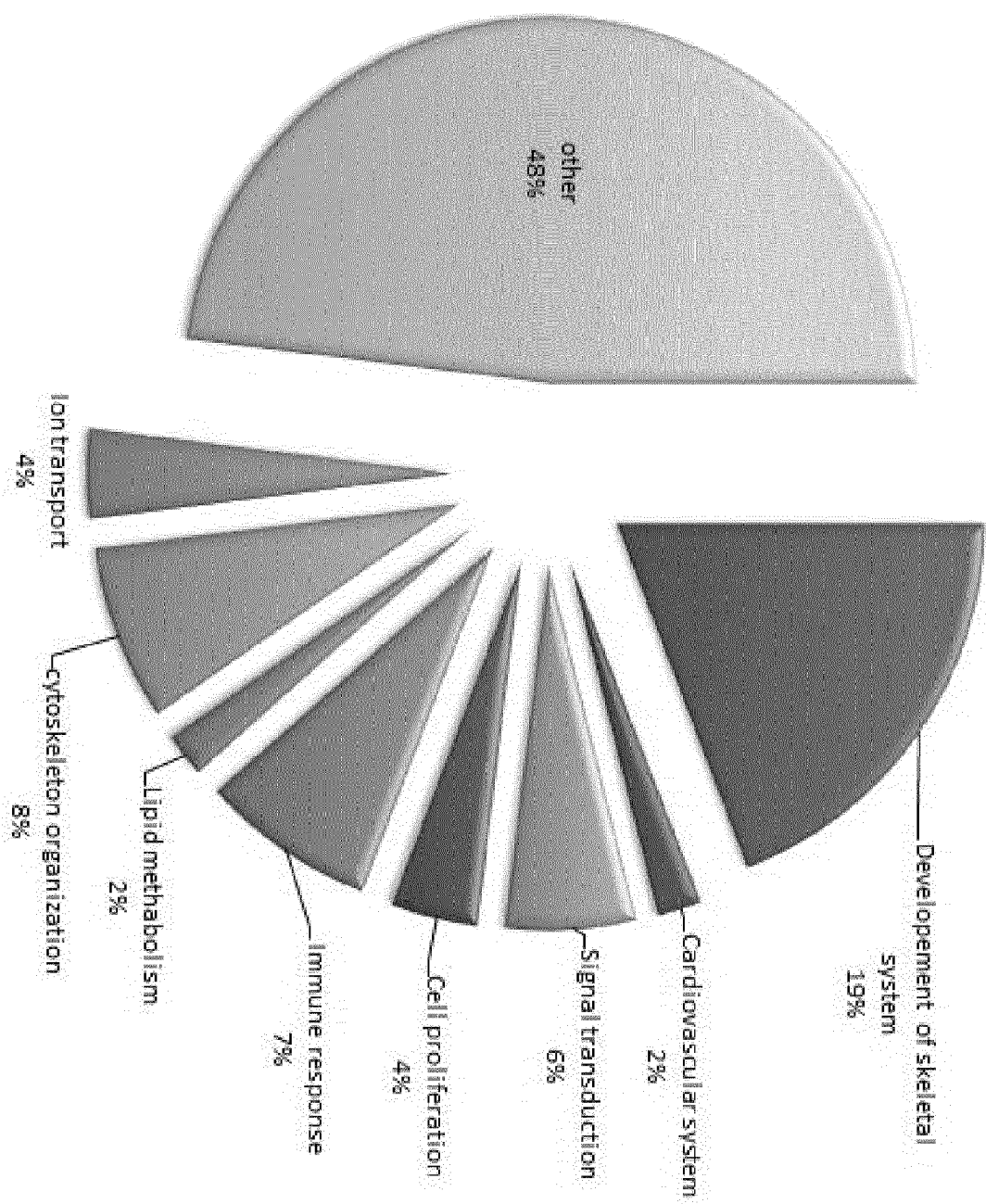
FIG. 8 shows DNA microarray analysis of hMSC-TERT under osteogenic culture conditions, in the presence or absence of H-8. 19% of the genes that the present were up or down regulated more than two folds, 24 hours after H-8 treatment (25 µM), are known to be involved in development skeletal system.
Figure 9:
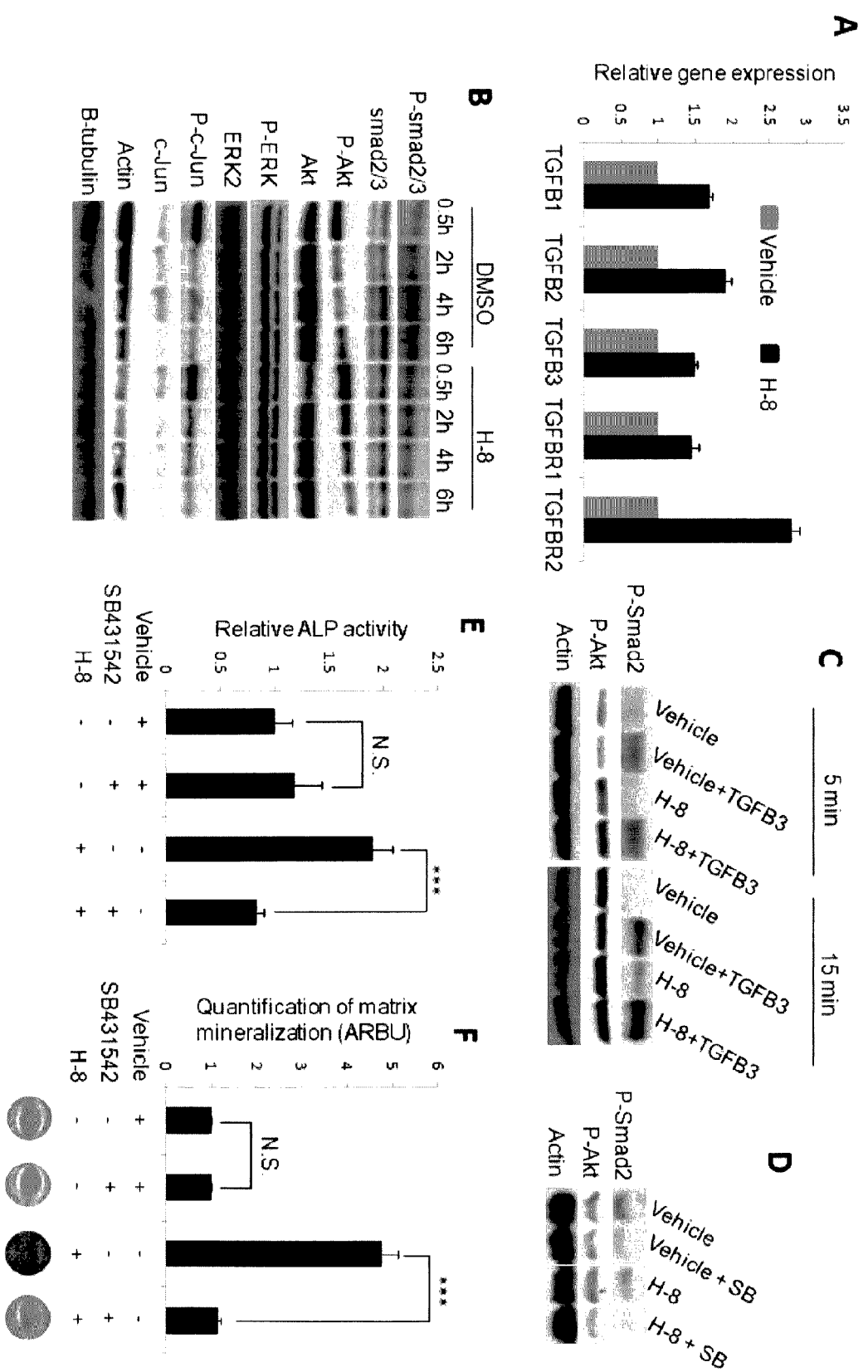
FIG. 9 shows that the enhancing effect of H-8 on osteoblast differentiation of hMSC is mediated through activation of non-canonical TGFβ signaling. (A): qRT-PCR showed that treatment of hMSC with H-8 leads to enhanced expression of several components of TGFβ signaling. (B): Western blot analysis of different components of canonical (p-Smad2) and non-canonical (p-Akt, p-ERK, p-c-Jun) TGFβ signaling showed that H-8 treatment of hMSC leads to differential regulation of both canonical and non-canonical TGFβ signaling pathways. (C): Western blot analysis of p-Smad and p-Akt reveled that the enahcing effect of H-8 on osteoblast differentiation of hMSC is mediated through activation of non-canonical TGFβ signaling. (D): SB431542, a selective inhibitor of TGWU activity abolished the enhanced phosphorylation of Akt and smad2 after H-8 treatment. (E, F): SB431542 blunted the enhancing effect of H-8 on osteoblast differentiation of hMSC as shown by reduced ALP activity and matrix mineralization. *P≤0.05 (significant difference as compared to control).

H-8 Mediates it's Enhancing Effect on Osteoblastogenesis Through Regulation of TGFβ/BMP Signaling To investigate the mechanisms of the enhancing effects of H-8 on osteoblast differentiation of hMSC, the present inventors performed a DNA microarray analysis of hMSC-TERT under osteogenic culture conditions, in the presence or absence of the H-8 (25 µM). The present inventors found that 52 genes exhibited a significant up or down regulation of at least 2 folds, 24 hours after H-8 treatment. Among these, 19% are known to be skeletal development genes (FIG. 8) and genes related to Transforming Browth Factor β (TGFβ) signalling pathway were among the most significantly up-regulated genes. Increased expression of TGFβ1, TGFβ2, TGFβ3, TGFβR1, and TGFβR2 genes after H-8 treatment was further confirmed by qRT-PCR (FIG. 9A). Western blot analysis of different components of canonical TGFβ (Smad2) and non-canonical TGFβ (Akt, Erk, C-Jun) signaling revealed that H-8 treatment enhances phosphorylation of both canonical and non-canonical TGFβ signaling at different time points after H-8 treatment of hMSC (FIG. 9B). In order to identify the pathway that is primarily regulated by H-8 treatment, phosphorylation of canonical and non-canonical TGFβ signaling components was evaluated 5 minutes and 15 minutes after H-8 treatment. The inventors also evaluated the effect of TGFβ3 treatment on H-8 induced phosphorylation of Smad2 and Akt. H-8 treatment enhanced Akt phosphorylation at both 5 and 15 minutes after H-8 treatment, whereas enhanced Smad2 phosphorylation was detected only 15 minutes after H-8 treatment. Interestingly, TGFβ3 showed an enhancing effect on H-8 induced Akt and Smad2 phosphorylation (FIG. 9C). These observations suggest that the effect of H-8 treatment on hMSC is mediated primarily through activation of non-canonical TGFβ signaling. Furthermore, the inventors showed that SB431542 (SB), a selective small molecule inhibitor that blocks TGFβ signaling through inhibition of TGFβR activity, abolished the enhancing effect of H-8 on Smad2 and Akt phosphorylation (FIG. 9D) and blunted the enhancing effect of H-8 on osteoblast differentiation of hMSC, as shown by reduced ALP activity and reduced matrix mineralization (FIG. 9E, 9F). This observation further confirms that the enhancing effect of H-8 on osteoblast differentiation of hMSC is mediated through regulation of TGFβ signaling.

Discussion

Screening of the small molecule kinase inhibitor library identified several kinase inhibitors that regulated ALP activity. Among those, H-8 was found to have a strong and reproducible enhancing effect on ALP activity, during osteoblast differentiation of hMSC-TERT, primary MSC isolated from human bone marrow or adipose tissue. Further in vitro and in vivo studies showed that H-8 treatment enhances in vitro osteoblast differentiation and in vivo heterotopic bone formation of hMSC-TERT. H-8 is an ATP-competitive protein kinase inhibitor that inhibits protein kinase A (PKA) and protein kinase G (PKG) selectively over protein kinase C(PKC) and Myosin Light Chain Kinase (MLCK) ($IC_{50}$'s=1.2 µM, 0.48 µM, 15 µM and 68 µM respectively). Considering the fact that PKA, PKC, and PKG are important kinases that play a central role in many cellular processes, one may think that inhibiting the activity of these kinases will have toxic effects on the cells. However, on the contrary, the present inventors showed that H-8 treatment increaed hMSC survival in vitro and in vivo. It has been estimated that during the bone formation phase of bone remodeling, 50 to 70% of the osteoblasts undergo apoptosis. The fact that H-8 increases the hMSC survival during osteoblast differentiation has an important clinical application for settings in which increased bone formation is needed. Since the anti-apoptotic effect of PI3K/AKT pathway in osteoblasts and other cell types have been reported before, the present inventors believe that reduced apoptosis of hMSC after H-8 treatment, is due to the activation of PI3K/AKT signaling, as shown by western blot analysis of phospho-AKT after H-8 treatment. However, the enhancing effect of H-8 on differentiation was found to be specific, since it only enhanced differentiation of hMSC toward osteoblast, but not adipocyte. The results from microarray analysis of gene expression, after H-8 treatment of hMSC, drew the attention toward TGFβ signaling and the further investigation of TGFβ signalling confirmed that the enhancing effect of H-8 on osteogenesis is mediated through activation of components of non-canonical TGFβ signalling pathway, which are known to positively regulate osteognesis.

One of the interesting observations in this study was that the effect of H-8 on enhancing osteoblast maturation was more apparent on non-differentiated stem cell population, rather than their differentiated progeny. From clinical point of view, this capacity is very important, since the currently available therapies for treatment of bone loss diseases, that are based on targeting mature cell populations like osteoblast and osteoprogenitors (using PTH administration) or osteoclasts (using bisphosphonates), have many intrinsic limitations. It has been shown that long-term osteoclast inhibition leads to inhibition of osteoblast activity as well, and bisphosphonates have been recently implicated in osteonecrosis. Furthermore, in osteolytic disease of malignancy, osteoblasts are decreased in number and activity, thus diminishing the effect of any drug that targets osteoblasts. Therefore, the capacity to target the differentiation of more primitive populations of cells is very attractive in settings where mature cell populations have been depleted or have become dysfunctional.

Based on in vitro studies, the optimal concentration of H-8, to get the highest enhancement on osteoblast differentiation of hMSC, is around 20-30 µM. However, this range of concentration may not be suitable, if H-8 is to be developed into a novel drug, to be used systematically for treatment of osteoporosis. Therefore, finding analogues for H-8, which show the same enhancing effect on osteoblast differentiation of hMSC, but with lower effective molar concentration is highly desirable.

The invention claimed is:

1. A method of treating or preventing a degenerative bone disorder comprising:
administering to an individual in need thereof the compound comprising the formula:

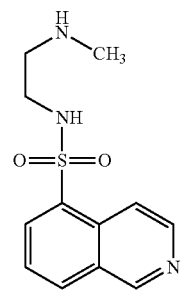

wherein the chemical formula is N-[2-(methylamino)ethyl]-5-isoquinolinesulfonamide or a pharmacologically acceptable salt thereof and wherein the degenerative bone disorder is selected from a group consisting of endocrinopathy, hypercorticolism, hypogonadism, hyperparathyroidism, hypoparathyroidism, bone fracture, repair of bone defects, and repair of bone destruction following bone metastases.

2. A method of treating or preventing a degenerative bone disorder comprising:

administering to an individual in need thereof the compound comprising the formula:

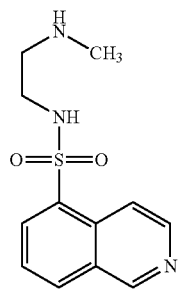 [SMILES: CNCCNS(=O)(=O)c1cccc2cnccc12]

wherein the chemical formula is N-[2-(methylamino)ethyl]-5-isoquinolinesulfonamide or a pharmacologically acceptable salt thereof and wherein the degenerative bone disorder is selected from a group consisting of osteodystrophy, osteopenia and a degenerative bone disorder caused by an imbalance of osteoclast and osteoblast activity that results in net excess of bone resorption over bone formation.

3. A method of treating or preventing a degenerative bone disorder by administering to an individual in need thereof a compound comprising the formula:

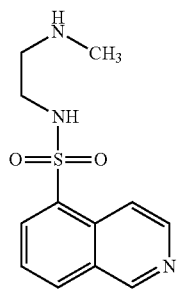

wherein the chemical formula is N-[2-(methylamino)ethyl]-5-isoquinolinesulfonamide or a pharmacologically acceptable salt thereof and wherein the degenerative bone disorder is selected from a group consisting of primary osteoporosis, postmenopausal osteoporosis, senile osteoporosis and juvenile osteoporosis.

4. The method of claim 1, wherein the administration is for use adjunctively with an antiresorptive agent.

5. The method of claim 1, wherein the pharmaceutically acceptable salt is dihydrochloride salt.

6. The method of claim 2, wherein the pharmaceutically acceptable salt is dihydrochloride salt.

7. The method of claim 3, wherein the pharmaceutically acceptable salt is dihydrochloride salt.

8. The method of claim 2, wherein the administration is for use adjunctively with an antiresorptive agent.

9. The method of claim 3, wherein the administration is for use adjunctively with an antiresorptive agent.

\* \* \* \* \*